United States Patent
Lopez

(10) Patent No.: US 6,585,714 B2
(45) Date of Patent: Jul. 1, 2003

(54) FOOLPROOFING DEVICE FOR A CONTAINER SUCH AS A CONTAINER INTENDED FOR MEDICAL USE

(75) Inventor: Joan Lopez, Mouans Sartoux (FR)

(73) Assignee: Tournaire S.A., Grasse (FR)

( * ) Notice: Subject to any disclaimer, the term of this patent is extended or adjusted under 35 U.S.C. 154(b) by 0 days.

(21) Appl. No.: 09/912,314

(22) Filed: Jul. 26, 2001

(65) Prior Publication Data

US 2003/0023226 A1 Jan. 30, 2003

(51) Int. Cl.[7] .......................... A61B 19/00; B65B 7/28; B65B 47/00; B65B 51/18
(52) U.S. Cl. .................. 604/403; 604/415; 215/43; 215/256; 220/253
(58) Field of Search ................................ 604/403, 415; 220/658, 253, 345.1; 215/43, 223, 256

(56) References Cited

U.S. PATENT DOCUMENTS

| 5,642,825 A | * | 7/1997 | Wohlgemuth | 215/256 |
| 5,718,346 A | * | 2/1998 | Weiler | 215/50 |
| 6,010,026 A | * | 1/2000 | Dekhoff et al. | 220/288 |
| 6,019,752 A | * | 2/2000 | Sunago et al. | 604/416 |

* cited by examiner

Primary Examiner—Henry Bennett
Assistant Examiner—Alfred Basichas
(74) Attorney, Agent, or Firm—James C. Lydon

(57) ABSTRACT

The invention relates to a foolproofing device (12) equipped with pins (14-1 and 14-2) placed around the neck of a container (10), the container containing a product for pharmaceutical, medical or other use intended to be used by an extraction system (30) screwed onto a threaded support which may be the neck of the container itself or a sleeve (16) placed on the neck of the container, the screwing operation and thus the use of the product by the extraction system being possible only if the notches (34-1 and 34-2) of the extraction system coincide with the pins of the foolproofing device. According to a main characteristic of the invention, the foolproofing device (12) is characterized in that it is integral with the threaded support (16) of the container by means of connecting parts (18) between the foolproofing device and the threaded support, the connecting parts being broken when the extraction system coinciding with the foolproofing device is screwed onto the threaded support of the container.

9 Claims, 3 Drawing Sheets

FOOLPROOFING DEVICE FOR A CONTAINER SUCH AS A CONTAINER INTENDED FOR MEDICAL USE

TECHNICAL FIELD

The present invention relates to a device placed on the neck of a container containing a product intended to be used by means of an extraction system on the neck of the container, enabling mechanical recognition of the system and the neck and thus the product in order to avoid incorrect handling and particularly concerns a foolproofing device for a container such as a container intended for medical use.

BACKGROUND ART

One can find products intended for pharmaceutical, medical or other uses which are similar in their applications but differ in their composition. They are contained in identical containers, and only the information on the label affixed on the container enables one to tell them apart. In the case of anesthetic products used with a gravity-feed perfusion system, the container, with its cap removed, is placed in a high position, the opening being directed downward. The system, connected to a tube, is thus screwed directly onto the threaded neck of the container or onto a threaded sleeve placed on the neck of the container, in place of the cap, by means of a connector, so that the product flows from the container toward the patient to be treated by means of the tube. The visual check performed by the person setting up the perfusion system is the only measure that guarantees the correct use of the product.

In order to avoid incorrect handling attributable to human error, a foolproofing device exists in the form of a cylindrical ring which attaches to the neck of the container underneath the threads and designed to receive the container's cap. Along its circumference, the ring features identically shaped pins. There are at least two pins which are separated by an angular distance that varies according to the foolproofing device type. Two foolproofing devices are thus differentiated by the angle between the two pins. In this manner, there are as many foolproofing devices as there are products to be differentiated. The foolproofing device fits freely around the neck of the container so that it can rotate freely around the neck so as not to inhibit the perfusion system connector which screws onto the neck of the container.

The perfusion system is also equipped with a foolproofing device consisting of a female part designed to fit in its male counterpart placed on the container. In this manner, each perfusion system can be fitted with only one type of product. Correct product usage is thus guaranteed by "mechanical" recognition since this system only allows one type of container, and thereby one specific product, to be used for a given perfusion system.

The installation of the foolproofing device on the container is generally ensured by the company which fills the containers. This operation, which consists in fitting a specific part onto the neck of the container, represents an additional operation when the container is filled with the product. Furthermore, the foolproofing device turns freely around the neck when installed and thus its position is the same, whether or not the container has already been used. Thus, if the container is not fully emptied the first time it is used, it can be employed a second time without proof that it has already been used.

SUMMARY OF THE INVENTION

This is why the main purpose of the invention is to provide a foolproofing device which adapts onto the neck of a container and enables differentiation of the products contained in the container during their use by means of an extraction system, and which is integral with a threaded support such as a sleeve on the neck of the container, and thus placed on the neck at the same time as the sleeve.

Another purpose of the invention is to provide a foolproofing device integral with the container's sleeve such that the placement of the connector of the extraction system designed to remove the product from the container requires that the foolproofing device be first removed from the sleeve in order to guarantee the initial use of the container on its extraction system.

The object of the invention is thus a foolproofing device equipped with pins placed around the neck of a container, the container containing a product for pharmaceutical, medical or other use intended to be used by an extraction system screwed onto a threaded support which may be the neck of the container itself or a sleeve placed on the neck of the container, the screwing and thus the use of the product by the extraction system being possible only if the notches of the extraction system coincide with the pins of the foolproofing device.

According to a main characteristic of the invention, the foolproofing device is integral with the threaded support of the container owing to connecting parts between the foolproofing device and the threaded support, the connecting parts being broken when the extraction system coinciding with the foolproofing device is screwed onto the threaded support of the container.

According to an embodiment of the invention which is particularly advantageous, the container contains an anesthetic product and specifically a veterinary anesthetic product and the extraction system for the product contained in the container is a gravity-feed perfusion system.

BRIEF DESCRIPTION OF THE DRAWINGS

The purposes, objects and characteristics of the invention will become more apparent from the following description when taken in conjunction with the accompanying drawings in which.

DETAILED DESCRIPTION OF THE PREFERRED EMBODIMENT

Figure 1:
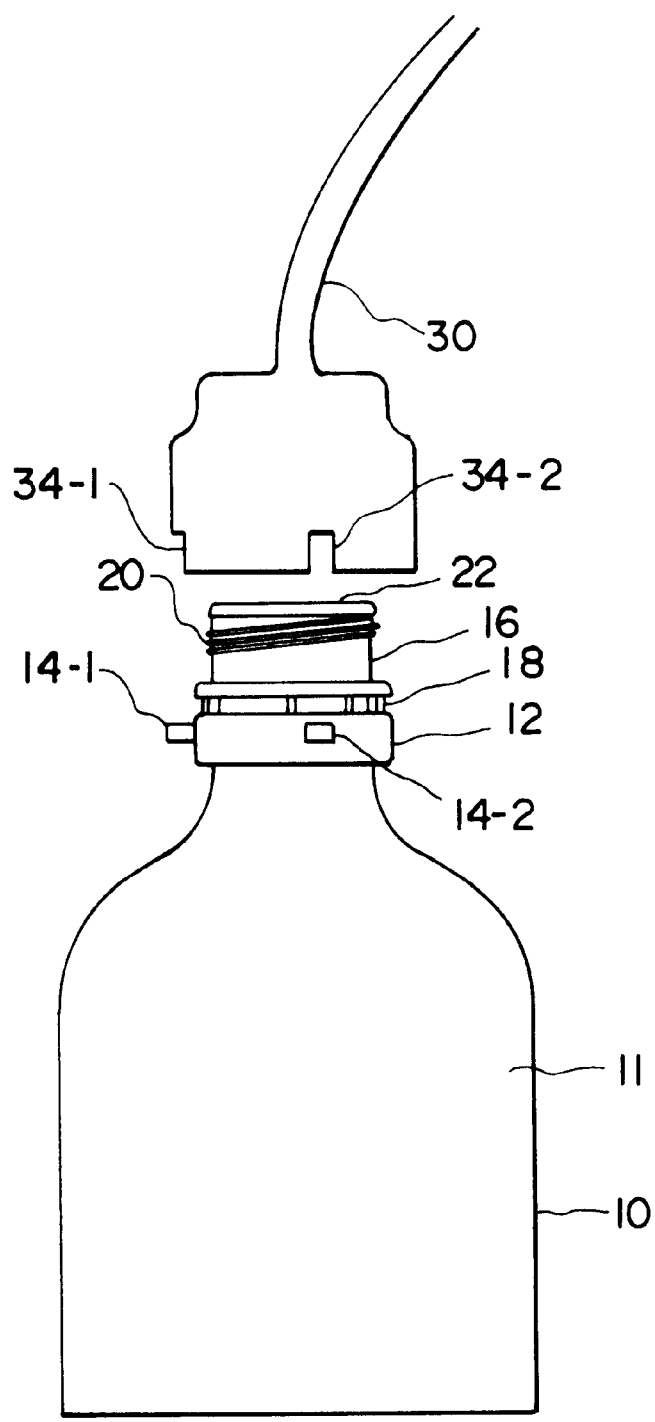
FIG. 1 represents the container equipped with the sleeve and the foolproofing device.

In FIG. 1, the container 10 that contains the product 11 intended for pharmaceutical or medical use, or other product such as a dangerous product, is made of plastic, glass or preferably aluminum. The neck of the container features a plastic part consisting primarily of a sleeve 16 equipped with threads 20, and a cylindrical ring 12. The sleeve 16 and the ring 12 are placed on the container 10 after the container has been manufactured. The sleeve 16 is retained on the container by means of a flanged lip formed by the neck of the container 10 having a "rolled" shape 22 on the sleeve 16. It should be noted that the threaded support 16 may be the neck of the container itself.

The threads 20 are designed to receive a cap, not shown in the figure, or a system 30 designed to extract the product contained in the container 10 such as a perfusion system. The extraction system 30 is equipped with a connector designed to be screwed onto the threading 20 and features a flat seal which is pressed against the rolled flange 22 of the neck of the aluminum container when the connector is screwed on, thereby ensuring the seal of the extraction system.

The cylindrical ring 12 represents the foolproofing system and features at least two pins 14-1 and 14-2 on its circumference. The foolproofing device 12 is attached to the sleeve 16 by connecting parts 18. When the user wants to connect the perfusion system or other extraction system to the container, he/she removes the cap from the container and positions the connector of the extraction system 30 on the neck of the container so that the notches 34-1 and 34-2 coincide with the pins 14-1 and 14-2 of the foolproofing device 12. When the female parts corresponding to the notches and male parts corresponding to the pins coincide, the threads 20 of the container and the threads of the extraction system 30 couple and the user can thus screw the extraction system onto the sleeve. This screwing maneuver breaks the connecting pieces 18 and thus disconnects the foolproofing system 12 from the sleeve 16. The rotation of the foolproofing system, thus rendered free around the neck of the container, allows the extraction system to be screwed completely onto the container until the flange 22 of the container's neck presses against the flat seal of the extraction system thereby sealing the assembly. If, by mistake, the user tries to connect an extraction system and a container which are not intended to be connected together, it is impossible to connect the extraction system onto the container and the foolproofing device remains integral with the sleeve.

Figure 2:
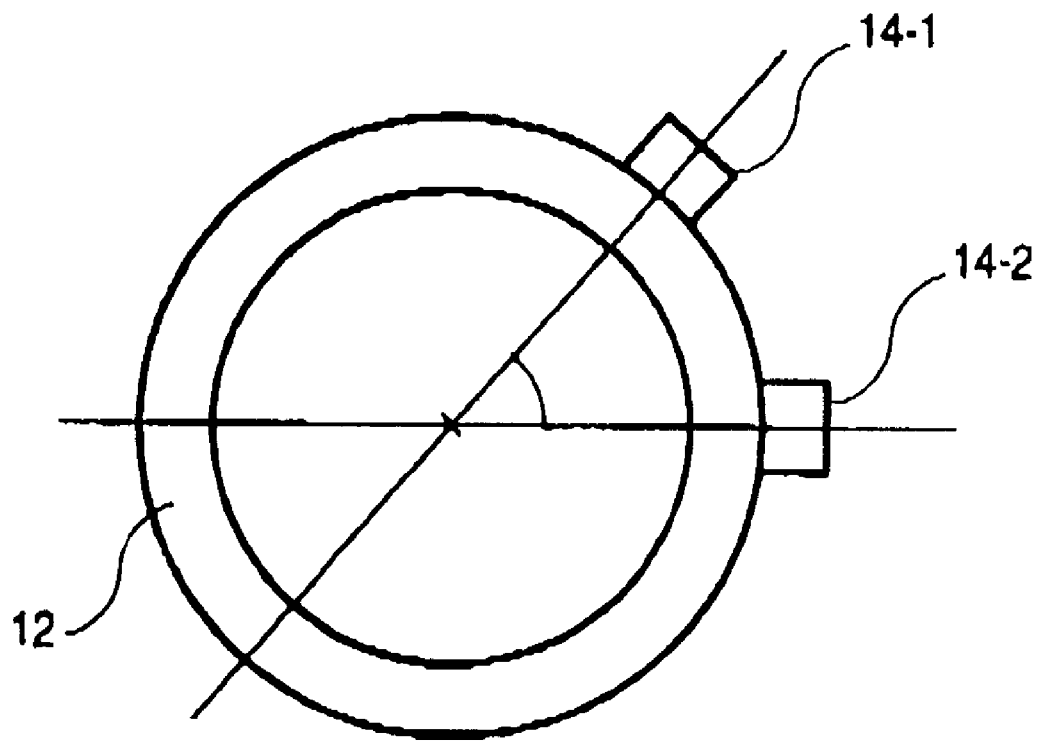
FIG. 2 is a top view of the foolproofing device.

As shown in FIG. 2, the foolproofing device 12 features at least two identical pins 14-1 and 14-2 angularly separated by an angle á. An angle á corresponds specifically to a foolproofing type and two foolproofing devices of a different type have a different angle á. The pins may have a different shape from one model to another or on a same foolproofing model without departing from the scope of the invention.

Figure 3:
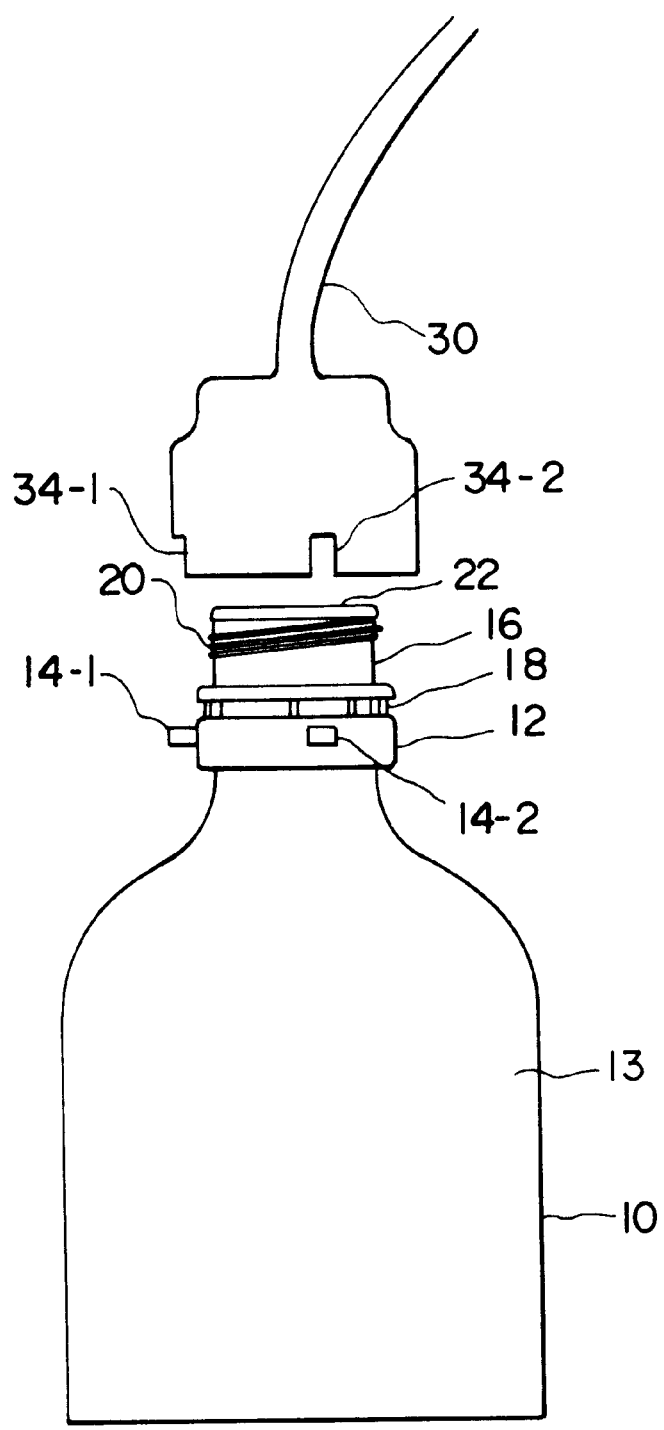
FIG. 3 represents the container equipped with the sleeve and the foolproofing device, and containing an anesthetic product.

FIG. 3 illustrates a container equipped with the sleeve and the foolproofing device similar to the container illustrated in FIG. 1. In this embodiment, container 10 contains an anesthetic product 13.

The present invention has the advantage of providing a container designed to contain a product intended for pharmaceutical, medical or other use, equipped with a foolproofing system on its neck designed to prevent incorrect handling when connected to a system for extracting the product contained in the container.

In addition, as the foolproofing system is detached from the sleeve when the container is attached to its extraction system, the user is thereby guaranteed that the container is being connected to its extraction system for the first time. In order to render tamperproof the product contained in the container equipped with a foolproofing device according to the invention, the container's cap may be equipped with a tamperproofing system, ensuring that it has not been previously opened. The tamper protection system may be any known system and particularly a system featuring connecting parts between the cap and the sleeve which are broken when the container's cap is unscrewed.

Furthermore, in an attempt to obtain total tamper protection of the container prior to its first use on the extraction system, a plastic membrane is place on the neck of the container after it is filled by a known means such as heat-sealing. When the container's cap is removed, the product contained in the container cannot spill out as long as the membrane is not pierced. When the connector of the extraction system coincides with the foolproofing device and is screwed onto the neck of the container to make the connection between the extraction system and the container, a slightly pointed piece forming part of the extraction system's connector for example, pierces the membrane at the end of the screwing operation so that the product flows freely from the container via the extraction system's connector.

What is claimed is:

1. A foolproofing device equipped with pins placed around the neck of a container, said container adapted to contain a product intended to be withdrawn from said container by an extraction system comprising notches, said extraction system being screwed onto a threaded support which is the neck of the container itself or a sleeve placed on the neck of the container, the screwing and thus withdrawal of the product by the extraction system is possible only if the notches of the extraction system coincide with the pins of the foolproofing device;

said foolproofing device being integral with said threaded support of the container thanks to connecting parts between said foolproofing device and said threaded support, said connecting parts being broken when the extraction system coincides with the foolproofing system screwed onto said threaded support of said container.

2. The foolproofing device according to claim 1, in which said container contains an anesthetic product and said extraction system of the product contained in said container is a gravity-feed perfusion system.

3. The foolproofing device according to claim 2, in which said pins, of which there are at least two, are placed on the circumference of said foolproofing device and separated angularly by an angle $\alpha$.

4. The foolproofing device according to claim 3 in which said container is made of aluminum.

5. The foolproofing device according to claim 4 in which said sleeve is placed on said container at the end of the manufacturing process of said container and blocked onto it thanks to a flange on the neck of said container which is rolled back onto said sleeve.

6. The foolproofing device according to claim 5 in which said container is equipped with a tamperproofing system comprising a cap and guaranteeing its first opening, made up of connecting parts between the cap of said container and said sleeve, said connecting pieces being broken when the cap on said container is unscrewed.

7. The foolproofing device according to claim 6 in which the neck of said container is covered after filling with a sealed membrane, said sealed membrane being pierced at the moment the extraction system is connected onto the threads of the container.

8. The foolproofing system according to claim 2, wherein said anesthetic product is a veterinary anesthetic product.

9. The foolproofing device according to claim 3, wherein said angle $\alpha$ is different for different products.

* * * * *